US00PP31683P3

(12) United States Plant Patent
Gray et al.

(10) Patent No.: US PP31,683 P3
(45) Date of Patent: Apr. 21, 2020

(54) FLORIBUNDA ROSE PLANT NAMED 'GRATGX'

(50) Latin Name: ***Rosa* hybrid**
Varietal Denomination: GRAtgx

(71) Applicants: John Charles Gray, Highfields (AU); Sylvia Elizabeth Gray, Highfields (AU)

(72) Inventors: John Charles Gray, Highfields (AU); Sylvia Elizabeth Gray, Highfields (AU)

( * ) Notice: Subject to any disclaimer, the term of this patent is extended or adjusted under 35 U.S.C. 154(b) by 0 days.

(21) Appl. No.: 16/350,969

(22) Filed: Feb. 6, 2019

(65) Prior Publication Data

US 2019/0254204 P1 Aug. 15, 2019

Related U.S. Application Data

(60) Provisional application No. 62/629,845, filed on Feb. 13, 2018.

(51) Int. Cl.
*A01H 5/02* (2018.01)
*A01H 6/74* (2018.01)

(52) U.S. Cl.
USPC ..... Plt./143
CPC ..... *A01H 6/749* (2018.05)

(58) Field of Classification Search
USPC ..... Plt./143
CPC ..... A01H 6/749; A01H 5/02
See application file for complete search history.

*Primary Examiner* — Keith O. Robinson
(74) *Attorney, Agent, or Firm* — Samuel R. McCoy, Jr.

(57) ABSTRACT

'GRAtgx' is a new and distinct floribunda type *Rosa* hybrid cultivar which is characterized by the combination of an upright to semi-weeping growth habit, good resistance to *Diplocarpon rosae* and *Podosphaera pannosa*, nearly continuous flowering, distinct cerise flowers with yellow stripes and flecks and a cream yellow reverse, a moderate rose fragrance, and the stability of these characteristics from generation to generation. The new cultivar is generally suited to landscape applications.

1 Drawing Sheet

Latin name of genus and species: The Latin name of the genus and species of the novel variety disclosed herein is *Rosa* hybrid.

Variety denomination: The inventive variety of *Rosa* hybrid disclosed herein has been given the variety denomination 'GRAtgx'.

BACKGROUND OF THE INVENTION

Parentage: 'GRAtgx' is a seedling selection which resulted from the controlled cross-pollination of an unnamed *Rosa* hybrid female breeding line (not patented) and an unnamed *Rosa* hybrid male breeding line (not patented). Both parents, developed by the same inventor and never commercially released, exhibited traits deemed commercially significant and desirable.

After many years of trialing, the female parent was confirmed to possess a combination of desirable traits such as high resistance to rose black spot disease, complete resistance to powdery mildew, and cerise pink flowers with yellow stripes and flecks and a yellow petal reverse, borne on a bushy plant growing to 1.2 m tall and wide. The male parent was selected for use in breeding after trialing confirmed the presence of a modern flower color. During the spring of 2014, the female parent was emasculated and was manually pollinated with pollen from the male parent. In autumn of 2015, seed was collected from hips produced by the female parent and a number of seedlings were grown to a mature size, including the claimed plant. These progeny were further evaluated for desirable traits such as black spot disease resistance and original flower color, and in January of 2016 the claimed plant was first observed. In January of 2017, after further evaluation for desirable traits, the claimed plant was deemed to be garden-worthy and suited to widespread cultivation. It was given the denomination, 'GRAtgx'.

Asexual Reproduction: Asexual propagation of 'GRAtgx', by way of softwood stem cuttings, was first performed in May of 2016 at the inventor's nursery in Highfields, Australia. Through more than twelve subsequent generations, the unique features of this cultivar have proven to be stable and true to type.

SUMMARY OF THE INVENTION

The following characteristics have been repeatedly observed and represent the distinguishing characteristics of the new *Rosa* cultivar 'GRAtgx'. These traits, in combination, distinguish 'GRAtgx' as a new and distinct cultivar.

1. *Rosa* 'GRAtgx' exhibits an upright to semi-weeping growth habit; and
2. *Rosa* 'GRAtgx' exhibits high resistance to the plant pathogen, *Diplocarpon rosae*, commonly referred to as rose black spot disease; and
3. *Rosa* 'GRAtgx' exhibits nearly continuous flowering; and
4. *Rosa* 'GRAtgx' exhibits a double flower type; and
5. *Rosa* 'GRAtgx' exhibits cerise pink flowers with yellow stripes and flecks and a yellow petal reverse; and
6. *Rosa* 'GRAtgx' exhibits flowers with a moderate to strong rose fragrance.

BRIEF DESCRIPTION OF THE DRAWING

The FIGURE illustrates, as nearly true as it is reasonably possible to make the same in color photographs of this type, the typical flower of 'GRAtgx'.

DETAILED BOTANICAL DESCRIPTION

The following observations and measurements, made in February of 2018, describe averages of two own-root specimens of one year old 'GRAtgx' plants. The plants were grown outdoors in a garden bed of a red krasnozem soil in full sunlight, at the inventor's nursery in Highfields, Australia. No shade or supplemental light was provided. Temperatures ranged from approximately 17 to 35 degrees Celsius during the day and 7 to 18 degrees Celsius at night. Standard practices for irrigation, fertilizer and pest control were applied at appropriate times during the growing season. The plants were pruned three times during the growing season using accepted techniques for rose pruning.

Those skilled in the art will appreciate that certain characteristics will vary with older or, conversely, with younger plants. 'GRAtgx' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2007 Fifth Edition except where common terms of color are used.

A botanical description of 'GRAtgx' and comparisons with the parents and the most similar commercial cultivar of *Rosa* hybrid are provided below.

General plant description:

*Growth habit.*—Upright to semi-weeping.

*Growth rate.*—Approximately 6 months to reach 60 cm.

*Dimensions.*—60 cm tall and 50 cm wide.

*Environmental tolerance.*—Very good heat tolerance; cold hardiness is unknown.

*Disease resistance.*—Excellent resistance to powdery mildew (*Sphaerotheca pannosa*) and good resistance to blackspot (*Diplocarpon rosae*).

*Propagation.*—Technique — Softwood stem cuttings. Time to initiate roots — About 13 days at approximately 21 degrees Celsius at root zone and 18 degrees Celsius ambient temperature. Time to produce a rooted cutting — About 25 days at approximately 21 degrees Celsius at root zone and 18 degrees Celsius ambient temperature.

Root system: White fibrous roots with many root hairs extending from lesser roots in a featherlike arrangement.

Branches:

*Branching habit.*—Irregular branching from mature branches, breaking first from the uppermost buds near the apex of each shoot.

*Quantity.*—Numerous.

*General dimensions.*—Approximately 35 cm long; 1.5 cm in diameter near the base and tapering to 1.0 cm.

*Immature branches.*—Diameter — Approximately 0.5 cm. Texture and pubescence — Smooth with prickles; glabrous. Color — Near RHS 135D. Prickles — Density — Sparse to moderate. Color — Near RHS 29C. Shape — Convex. Texture — Smooth.

*Mature branches.*—Diameter — Approximately 1.5 cm, after one year. Texture and pubescence — Smooth with prickles; glabrous. Color — Near RHS 145B. Prickles — Density — Sparse to moderate. Color — Near RHS 164A. Shape — Convex. Texture — Smooth.

Leaves:

*Arrangement.*—Alternate imparipinnate compound leaves.

*Quantity.*—Approximately 5 per mature branch.

*Attachment.*—Petiolate.

*Leaf internode length.*—4 cm.

*Dimensions.*—Approximately 12 cm long and 10 cm wide.

*Petiole.*—Dimensions — 3.0 cm long and 0.1 to 0.2 cm wide. Color — Near RHS 145A and margined RHS 143B. Texture and pubescence — Smooth and glabrous. Prickles — Present. Stipitate glands — Not present.

*Stipule.*—Dimensions — 2.0 cm long and 0.5 cm wide. Color — Near RHS 150B. Texture and pubescence — Smooth and glabrous. Margins — Ciliate. Apex — Apiculate. Base — Winged. Prickles — Not present. Stipitate glands — Not present.

*Rachis.*—Dimensions — 2.3 cm long and 0.1 cm wide. Color — Near RHS 145A. Prickles — Present. Stipitate glands — Not present.

*Leaflets.*—Quantity — Seven leaflets on axillary leaves. Dimensions — Average size of the terminal leaflet is 4 cm long and 5 cm wide. Shape — Ovate. Apex — Acuminate. Base — Ovate. Margins — Serrated. Texture, pubescence and luster, adaxial surface — Smooth, glabrous, and glossy. Texture, pubescence and luster, abaxial surface — Smooth, glabrous, and matte. Juvenile foliage color, adaxial surface — Near RHS 136B, with no anthocyanin intonations. Juvenile foliage color, abaxial surface — Near RHS 138C, with anthocyanin intonations. Mature foliage color, adaxial surface — Near RHS 141A. Mature foliage color, abaxial surface — Near RHS 135D. Venation — Pinnate. Venation color, adaxial surface — Near RHS 141B, with midrib RHS 144B. Venation color, abaxial surface — Near RHS 145B, with midrib RHS 142B. Petiolule — Dimensions — 0.4 cm long and 0.1 cm wide. Color — Near RHS N144 with no anthocyanin intonations present. Prickles — Not present. Texture — Smooth.

Inflorescence:

*Inflorescence type.*—Flowers are clustered.

*Blooming habit.*—Almost continuous from October through June in the southern hemisphere.

*Time to flower.*—6 to 8 weeks for a new stem to mature and flowering begins to occur once a stem matures.

*Peduncle.*—Dimensions — 15 cm long and 0.5 cm in diameter. Color — Near RHS 145A. Strength — Rigid. Texture and pubescence — Smooth and glabrous. Prickles — Not present.

Bud:

*Shape.*—Ovate.

*Size.*—2.0 cm long and 1.5 cm in diameter.

*Color.*—Near RHS 142B.

Flower:

*Calyx*.—General — Comprised of five polysepalous sepals. Diameter of calyx — 1.0 cm. Sepals — Color, interior surface — RHS 142D. Color, exterior surface — RHS 144A. Dimensions — 2.5 cm long and 1.0 cm wide. Apex — Apiculate. Base — Flat at union with receptacle. Quantity — Five. Pubescence — Densely puberulent. Margins — Entire. Stipitate glands — None present.

*Corolla*.—General shape of corolla — Cupped and irregularly-rounded with a tight outer whorl. Rate of opening — 6 days from bud to anthesis. Dimensions — Approximately 6 cm in diameter and 5 cm deep. Fragrance — Moderate rose scent. Lastingness — On the plant for 5 days after anthesis. Persistence — Self-cleaning. Petals — Petal count — Exhibits double flowers with approximately 25 petals under normal conditions. Petal arrangement — Irregularly rounded whorl at anthesis and aging to a loose whorl. Dimensions — 4.5 cm long and 5.0 cm wide. Petal shape — Obovate. Apex — Rounded. Base — Flattened, then obtuse. Petal reflex — Slightly reflexed at apex. Petal margin — Entire; slightly undulating. Texture — Soft. Aspect — Formal. Petal color, upon opening — Upper surface — Near RHS 45A with base near RHS 9A, striped and flecked near RHS 12A. Lower surface — Near RHS 8C with base near RHS 9A. Petal color, at anthesis — Upper surface — Near RHS N66A with base near RHS 9A. Lower surface — Near RHS 8C with margin near RHS 9A. Fading — Near RHS 54C.

Reproductive organs:

*Stamens*.—Quantity — Approximately 50. Anthers — Shape — Narrow ovate. Length — 1.0 cm. Color — Near RHS 12B. Pollen — Abundant. Pollen Color — Near RHS 3A. Filaments — Color — Near RHS 17C. Length — Approximately 0.8 cm.

*Pistils*.—Quantity — Approximately 50. Length — Approximately 1.0 cm. Stigma — Shape — Ovate. Color — Near RHS 11B. Style — Length — Approximately 0.8 cm long. Color — Near RHS 18C.

*Ovary*.—Dimensions — 0.5 cm long and 0.3 cm wide. Color — Near RHS 3D.

*Receptacle*.—Shape — Pitcher-shaped. Dimensions — 0.5 cm high and 0.5 cm wide. Color — Near RHS 141D.

Hip and seed:

*Hip*.—Shape — Rounded. Dimensions — 1.0 cm long and 1.0 cm wide. Texture — Smooth. Color — Near RHS 135D.

*Seed*.—Shape — Rounded. Dimensions — 1.0 cm long and 1.0 cm wide. Color — Near RHS 144D.

Comparisons with the parents: The new rose plant 'GRAtgx' may be distinguished from its seed parent, an unnamed breeding line (not patented), by the following combination of characteristics: 1. 'GRAtgx' exhibits cerise flowers with yellow stripes and flecks and a cream yellow reverse, whereas the flowers of the seed parent exhibit a white general coloration. 2. 'GRAtgx' exhibits an upright to semi-weeping growth habit, whereas the seed parent exhibits an upright growth habit. The new rose plant 'GRAtgx' may be distinguished from its pollen parent, an unnamed breeding line (not patented), by the following combination of characteristics: 1. 'GRAtgx' exhibits cerise flowers with yellow stripes and flecks and a cream yellow reverse, whereas the flowers of the pollen parent exhibit a dark red general tonality with coffee stripes. 2. 'GRAtgx' exhibits an upright to semi-weeping growth habit, whereas the pollen parent exhibits an upright growth habit.

Comparisons with the most similar variety of common knowledge: Plants of the new cultivar 'GRAtgx' may be distinguished from the commercial variety *Rosa* hybrid 'WEKplapep' (U.S. Plant Pat. No. 10,126) by the following combination of characteristics: 1. 'GRAtgx' exhibits cerise flowers with yellow stripes and flecks and a cream yellow reverse, whereas the flowers of 'WEKplapep' are red striped and flecked white. 2. Leaves of 'GRAtgx' are bullate and glossy mid-green, whereas leaves of 'WEKplapep' are glossy dark green. 3. 'GRAtgx' has flowers with moderate fragrance, whereas 'WEKplapep' flowers have strong fragrance with damask notes.

That which is claimed:

1. A new and distinct variety of *Rosa* hybrid plant named 'GRAtgx' as described and illustrated herein.

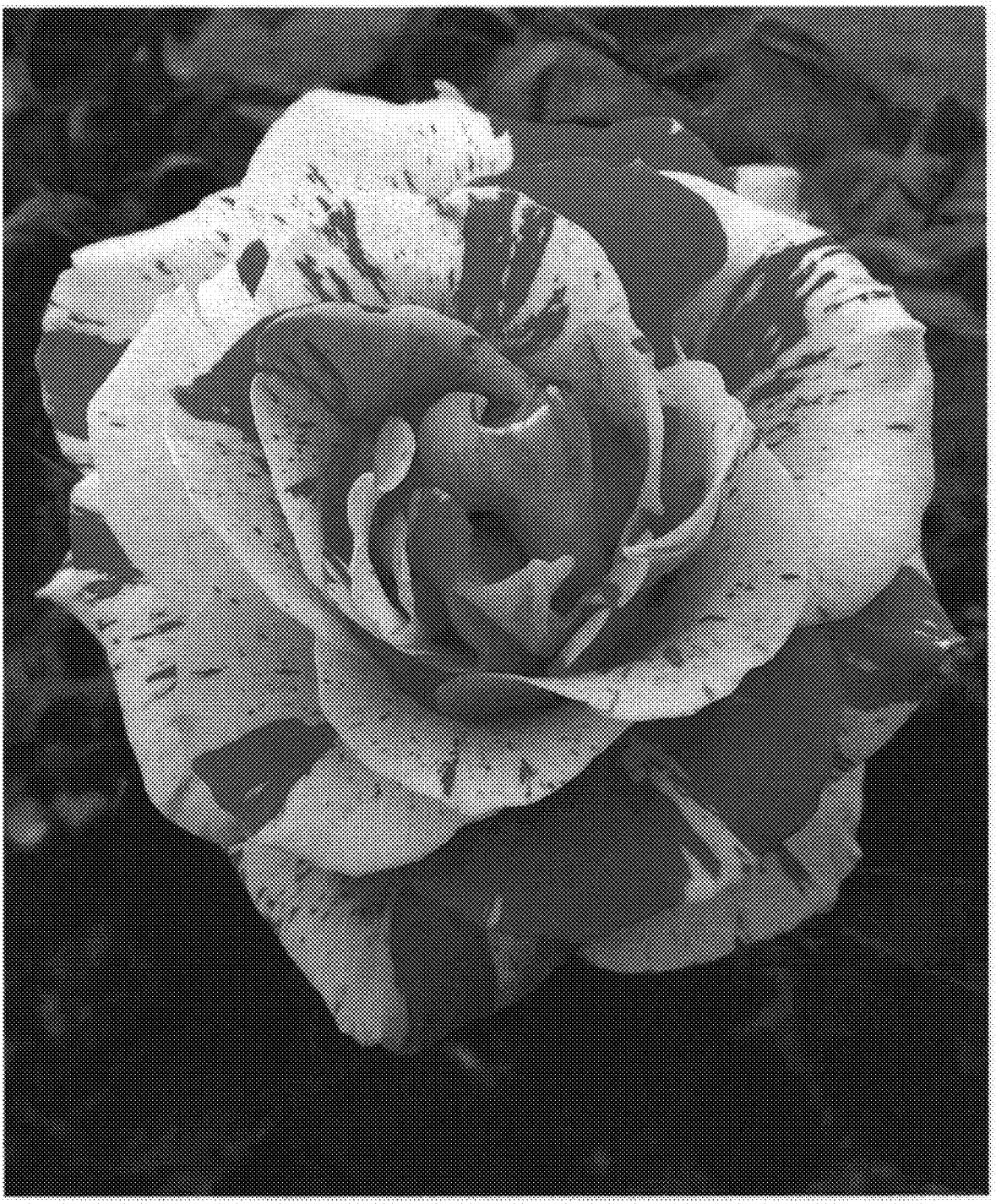

* * * * *